Figure 1:
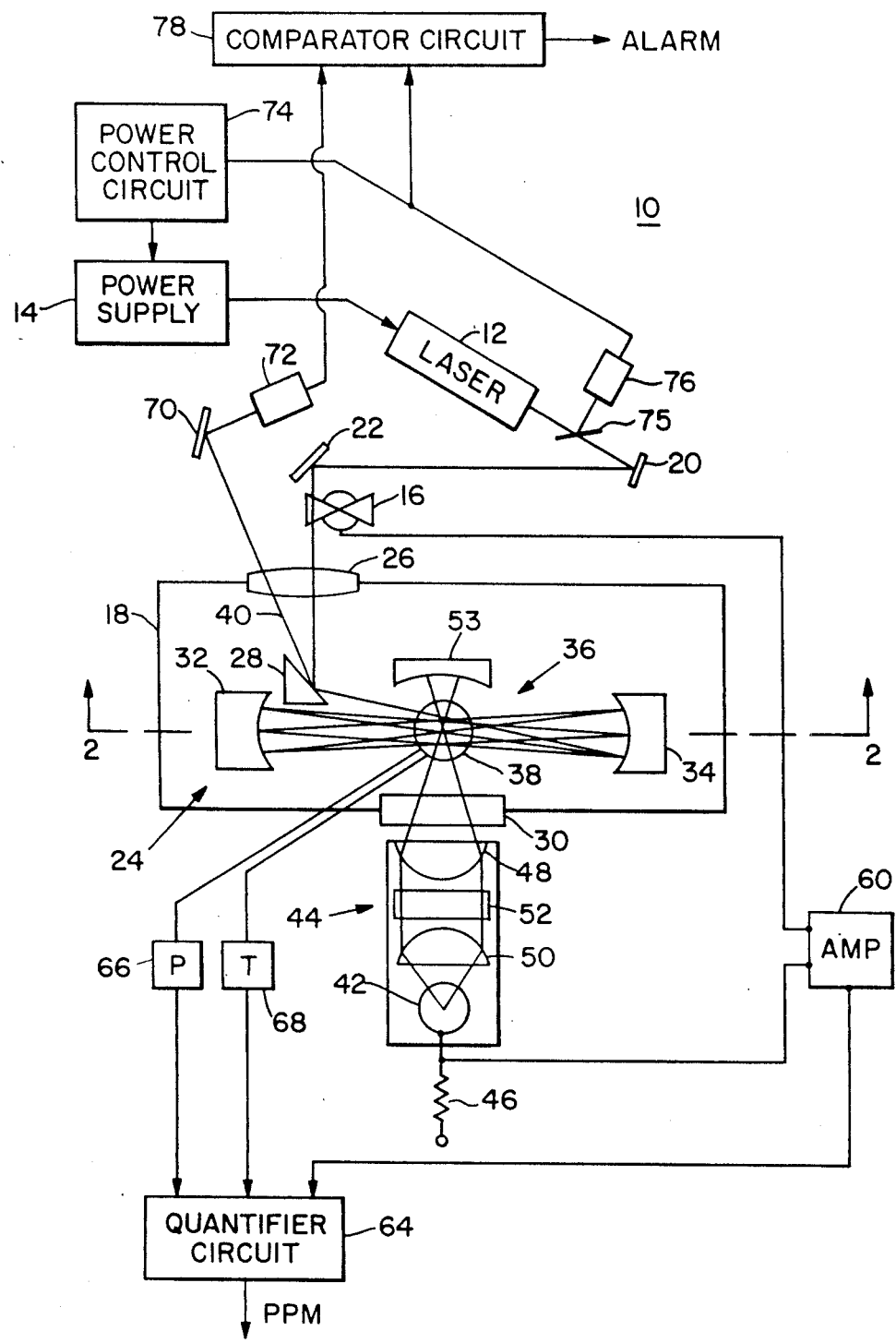

United States Patent [19]

Adler-Golden et al.

[11] Patent Number: 4,953,976
[45] Date of Patent: Sep. 4, 1990

[54] GAS SPECIES MONITOR SYSTEM

[75] Inventors: Steven Adler-Golden, Newtonville; Neil Goldstein, Medford; Fritz Bien, Concord, all of Mass.

[73] Assignee: Spectral Sciences, Inc., Burlington, Mass.

[21] Appl. No.: 325,981

[22] Filed: Mar. 20, 1989

[51] Int. Cl.$^5$ .......................... G01J 3/44; G01N 21/65
[52] U.S. Cl. ....................................... 356/301
[58] Field of Search ......................................... 356/301

[56] References Cited

U.S. PATENT DOCUMENTS

| | | | |
|---|---|---|---|
| 3,802,777 | 4/1974 | Regnier et al. | 356/301 |
| 3,906,241 | 9/1975 | Thompson | 356/301 |
| 4,127,329 | 11/1978 | Chang et al. | 356/301 |
| 4,630,923 | 12/1986 | Tans et al. | 356/301 |
| 4,648,714 | 3/1987 | Benner et al. | 356/301 |
| 4,784,486 | 11/1988 | Van Klagenen et al. | 356/301 |

Primary Examiner—F. L. Evans
Attorney, Agent, or Firm—Joseph S. Iandiorio

[57] ABSTRACT

A gas species monitor system includes a sample volume for receiving a gas to be monitored; an external, independent laser source; means for directing the laser radiation to the volume; a multipass optical cell, responsive to the means for directing, for multiplying the laser radiation intensity in the sample volume; means for continuously flowing the gas to be monitored through the sample volume; a narrow bandpass filter; means for collecting more than a steradian of Raman scattered radiation from the sample in the volume and directing the collected radiation in parallel through the narrow bandpass filter; and means responsive to the parallel radiation from the filter for detecting the Raman scattered radiation representative of the concentration of the species in the gas sample being monitored.

6 Claims, 2 Drawing Sheets

GAS SPECIES MONITOR SYSTEM

FIELD OF INVENTION

This invention relates to an improved gas species monitor system, and more particularly to a system of monitoring scattered radiation from a flowing gas sample, with enhanced scattered radiation collection and detection, and very fast system response.

BACKGROUND OF INVENTION

It is frequently necessary to detect the presence and even the concentration of a gas species. For example, the detection of even a small amount of hydrogen before the launch of a space vehicle portends a serious problem. The most common optical detection method, infrared absorption, cannot be used for hydrogen and other homonuclear diatomic molecules. For these and other molecules, detection of Raman scattered light is advantageous, owing to the inherent linearity of the signal and its independence from the background gas composition, pressure, and temperature. However, a problem inherent in Raman and other inefficient optical scattering methods is the need to have a strong illumination source and an efficient method of light collection.

Two methods of providing strong illumination are to use a powerful laser and/or to place the sample within the laser cavity. The former method requires a bulky, expensive laser. The latter design is inherently not stable or rugged, and requires constant active adjustment to maintain alignment. With the latter method, problems may be caused by dirty windows on the sample or reference chamber and refractive index gradients; the latter may prevent use for real-time monitoring of a flowing sample. In addition, if a problem occurs, the entire system must be replaced or dealt with as a unit due to the integral construction.

SUMMARY OF INVENTION

It is therefore an object of this invention to provide an improved gas species monitor system.

It is a further object of this invention to provide such a system which is lower in cost and weight.

It is a further object of this invention to provide such a system which is simple, rugged, and relatively easily aligned and maintained in alignment.

It is a further object of this invention to provide such a system which uses a conventional, independent, external laser source.

It is a further object of this invention to provide such a system which obtains a stronger Raman scattered radiation detection signal.

It is a further object of this invention to provide such a system which eliminates the need for a reference chamber and specimen.

It is a further object of this invention to provide such a system which has faster response time.

It is a further object of this invention to provide such a system which employs a continuous flow-through sampling technique.

It is a further object of this invention to provide such a system which collects more than a steradian of Raman scattered radiation.

It is a further object of this invention to provide such a system which uses two or three orders of magnitude lower laser intensity and has an order of magnitude cost advantage.

This invention features a gas species monitor system having a sample volume for receiving a gas to be monitored and an external independent laser source. There are means for directing the laser radiation to the sample volume and a multipass optical cell, responsive to the means for directing, for multiplying the laser radiation intensity in the sample volume. There are means for continuously flowing the gas to the sample volume with minimum mixing between the sample and the gas in the optical cell. There is a narrow bandpass filter and means for collecting more than a steradian of Raman scattered radiation from the sample in the volume and directing the collected radiation in parallel through the narrow bandpass filter. Means responsive to the parallel radiation from the filter detect the Raman scattered radiation representative of the concentration of the species in the gas sample being monitored.

In a preferred embodiment the bandpass filter has a bandpass frequency which differs from the laser frequency by the characteristic vibrational frequency of the species of interest. There may be means for maintaining a constant laser power in the sample volume, and means for sensing the intensity of the laser beam exiting the sample volume and for verifying the number of times the laser beam is passed through the sample volume. The means for maintaining constant laser power may further include control means responsive to the means for sensing for varying the power applied to the laser source. There may be means, responsive to the means for detecting the Raman scattered radiation, for determining the relative concentration of the detected species.

The means for collecting radiation may include a collection lens adjacent the sample volume for collecting and collimating more than a steradian of radiation. There may also be included reflecting means adjacent the sample volume opposite the collecting lens for directing additional Raman scattered radiation to the lens.

DISCLOSURE OF PREFERRED EMBODIMENT

Figure 2:
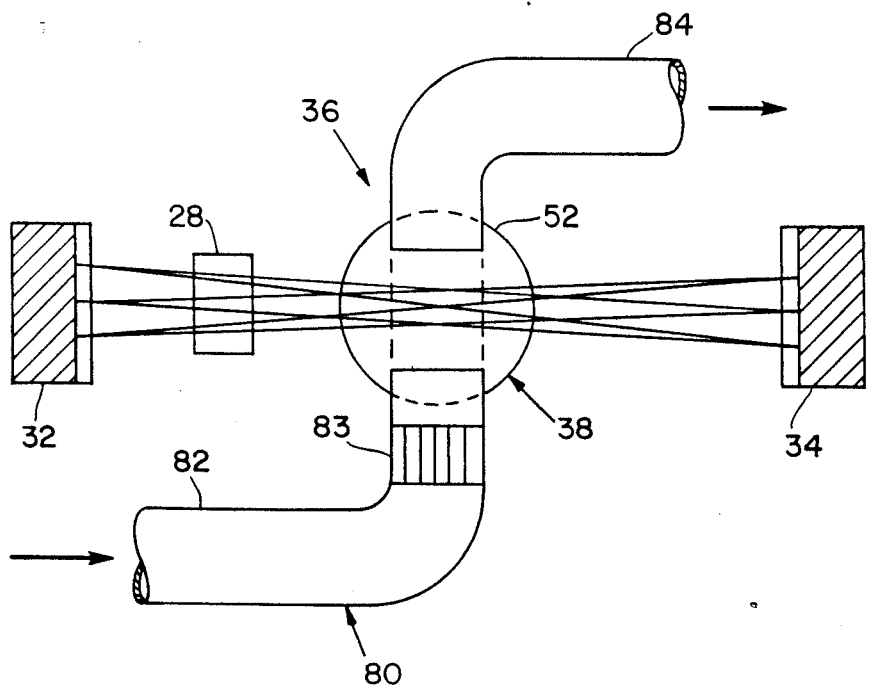

Other objects, features and advantages will occur to those skilled in the art from the following description of a preferred embodiment and the accompanying drawings, in which:

FIG. 1 is a schematic diagram of a gas species monitor according to this invention; and FIG. 2 is an enlarged detailed schematic view of the flow through sample volume assembly in the optical cell of the system of FIG. 1.

Although this invention applies to the detection of many different gas species, it was developed in response to the need for a reliable low-maintenance hydrogen gas detector to check for flammability conditions that may be encountered in the launch of space vehicles. The monitor system required a range of approximately 0.1 to 12% hydrogen and had to be operable in air, hydrogen, helium, or changing mixtures of all three without loss of accuracy. The current systems are not sufficiently reliable, particularly above four percent hydrogen and in helium background gas.

The system of this invention can accurately measure hydrogen concentration over a wide range of concentration (0.02-100%) and background gas composition. The system uses the technique of Raman light scattering to identify the hydrogen and measure its concentration. The system uses monochromatic light from a laser, for example a helium neon or argon ion laser, which is passed through a sample volume containing a sample of the gas to be analyzed. The Raman scattered radiation generated by the hydrogen in the sample is shifted in wavelength by a characteristic amount. This shifted radiation is detected by a photomultiplier tube and the signal is converted into hydrogen concentration.

The Raman scattering technique has advantages over alternative approaches. The Raman scattered radiation is exactly proportional to the concentration and is unaffected by the composition of the background gas. These properties make calibration of the system simple and reliable. All components in the system are readily available and relatively inexpensive. Continuing advances in the size, cost and reliability of visible laser systems make this approach highly practical. Further, no expendables other than electric power are required for instrument operation. A suitable argon ion laser is the Omnichrome 532-AT, which has been rated at ten thousand hours of continuous operation at ten milliwatts and operates at a wavelength of 488 nm.

Gas species monitor 10, FIG. 1, according to this invention includes laser 12 driven by power supply 14. Radiation from laser 12 is directed through chopper wheel 16 into optical cell chamber 18 by mirrors 20 and 22 which direct the beam into the optical cell 24. Entrance lens 26 focusses the incoming laser beam onto steering mirror 28 and into the center of the optical cell 24. Exit window 30 is typically a colored glass filter which passes the hydrogen Raman wavelength but blocks the transmission of scattered laser radiation.

The multipass optical cell 24 inside chamber 18 is a Herriott-type cavity defined by a pair of concave mirrors 32, 34, dielectrically coated for a 99.9% reflectivity of the laser wavelength. Mirrors 32 and 34 are placed at a distance of just under twice their radius of curvature, which is typically two to four inches, yielding a focal region 36 in the center of optical cell 24 where the laser beam repeatedly crosses the optical axis. This focal region 36 corresponds generally to sample volume 38 to provide the intense illumination of the gas sample in the sample volume necessary for observation of hydrogen Raman scattered radiation.

The laser beam is introduced into the optical cell 24 using the front surface reflective prism 28. As the beam repeatedly traverses optical cell 24, typically ten to forty times, it forms a circle or ellipse of spots on each of mirrors 32 and 34 before it is re-intercepted by prism 28 and passed out of chamber 18 through the entrance lens 26. The exiting beam 40 is well collimated and serves as an indicator of optical alignment as will be indicated subsequently.

The number of optical cell traversals is controlled by the distance between mirrors 32 and 34. The direction of the incoming beam determines the shapes and sizes of the ellipses and focal region 36. With the ellipses flattened nearly to a line in the vertical dimension, the focal region 36 is less than a millimeter high and five millimeters deep, which is small enough to be entirely imaged into the photocathode of the photomultiplier tube 42 in the collector.

The Raman radiation from sample volume 38 is directed to photomultiplier tube 42 by the collection optics 44. Tube 42 may be a Hamamatsu R955 multi-alkali tube. The output occurring from the photomultiplier is converted to a voltage using a terminating resistor 46. Discrimination of the hydrogen Raman signal from the scattered laser light, Raman scattering from the carrier gases, and background fluorescence, is accomplished by a 10 nm bandpass interference filter 52 inserted between lenses 48 and 50. For hydrogen monitoring, the filter is centered at 612 nm or 850 nm when used with the argon ion and helium-neon lasers, respectively. Collection of the Raman light is done using a 50 mm diameter, 38 mm focal length, aspheric collection lens 48 which collimates the Raman light, a 50 mm diameter, 62 mm focal length, biconvex lens 50, which focusses the light onto the photocathode.

The collection of Raman light is further enhanced by placing a 50 mm diameter, 19 mm focal length, aluminum coated concave reflector 30 directly behind the focal region 36 so as to direct an additional steradian of rear scattered Raman light back through the focal region and toward the collection optics 44. This adds to the approximately one steradian of light normally collected by lens 48.

Since the laser beam is chopped by chopper 16, the signal from the photomultiplier appears as a square wave. This signal is processed using a lock-in amplifier 60 which is referenced to chopper wheel 16, thereby suppressing the DC voltage arising from the photomultiplier dark current. The output of the lock-in amplifier is directly proportional to hydrogen concentration, and may be displayed on any suitable equipment such as a chart recorder or may be acquired by a computer for further processing.

Having determined the concentration of the hydrogen gas or other species present in the sample volume 38, the relative concentration of the species in parts per million can now be calculated. This is done by providing the concentration value to a quantifier circuit 64, multiplying the concentration by the temperature in the sample volume 38, and dividing it by the pressure in the sample volume 38, using inputs from pressure-sensing circuit 66 and temperature-sensing circuit 68.

Since system 10 does not use a reference species, the laser intensity in the focal region 36 must be monitored or maintained. In the preferred embodiment, a portion of the laser beam is sampled using beamsplitter 75 and directed onto sensor 76. A representation of this intensity is delivered to power control circuit 74 which determines whether the output intensity of laser 12 should be increased, decreased or left unchanged in order to maintain a pre-chosen intensity value and a suitable signal is delivered to direct power supply 14 accordingly. In an alternative embodiment, the signal from sensor 76 may be delivered to quantifier circuit 64 to normalize the concentration to the laser intensity. This is done by dividing the concentration by the signal from detector 76 and multiplying by a pre-stored value representing the detector 76 signal at the time of the instrument calibration.

A second intensity sensor 72 is positioned so that after a predetermined number of reflections the exiting beam 40 will precisely strike mirror 70 to be redirected to sensor 72 which provides a representation of the laser intensity exiting the cell. The representation of the laser intensity exiting the cell is compared with the representation of the laser intensity from sensor 76 using comparator circuit 78. This circuit outputs an alarm or other fault indicator if the two representations differ by more than a pre-chosen amount. This serves to indicate if misalignment or fouling of the optics has occurred.

The flow-through nature of sample volume 38 in focal region 36 can be seen in more detail in FIG. 2. There sample volume 38 is shown as a part of a flow system 80 which receives the sample to be monitored at its lower end 82. The sample moves through flow straightener 83, through the sample volume 38 in the focal region 36, and exhausts at upper end 84. There is minimal mixing between gas in the chamber and the flow. This provides real time, ambient condition monitoring of a gas sample for a species of interest. There is no need to provide a pressurized sample source or a closed sample container of known volume, pressure and temperature within the optical cavity. Therefore, alignment is unaffected by changes in sample conditions, and the possibility of fouling the optical elements is greatly diminished.

Although specific features of the invention are shown in some drawings and not others, this is for convenience only as each feature may be combined with any or all of the other features in accordance with the invention.

Other embodiments will occur to those skilled in the art and are with the following claims:

What is claimed is:

1. A gas species monitor system comprising:
   a sample volume for receiving a gas to be monitored;
   an external, independent laser source:
   means for directing the laser radiation to said volme;
   a multipass optical cell, responsive to said means for directing, for multiplying the laser radiation intensity in the sample volume;
   means for sensing the intensities of the laser radiation at said laser source and in said multipass optical cell after the beam of laser radiation has made predetermined number of reflections in said multipass optical cell through said sample volume;
   means for comparing said intensities of the laser radiation at said laser source and in said multipass cell to determine whether a system fault is present;
   means, responsive to said means for sensing, for controlling the power output of said laser source to maintain a predetermined value of power output;
   means for continuously flowing the gas to be monitored through the sample volume;
   a narrow bandbass filter;
   means for collecting more than a steradian of Raman scattered radiation from the sample in the volume and directing the collected radiation in parallel through said narrow bandpass filter; and
   means, responsive to the parallel radiation from the filter, for detecting and quantifying scattered radiation representative of the concentration of the species in the gas sample being monitored.

2. The system of claim 1 in which said bandpass filter has a bandpass frequency which differs from the laser frequency by a characteristic vibrational frequency of the species of interest.

3. The system of claim 1 in which said means for continuously flowing includes a flow straightener.

4. The system of claim 1 furter including means, responsive to the means for detecting, for determining the absolute concentratin of the detected species.

5. The system of claim 1 in which said means for collecting radiation includes a collection lens adjacent the sample volume for collecting and collimating more than a steradian of Raman scattered radiation.

6. The system of claim 5 in which said means for collecting radiation further includes reflecting means adjacet the sample volume opposite said collection lens for directing additional Raman scattered radiation to said collection lens.

* * * * *

UNITED STATES PATENT AND TRADEMARK OFFICE
CERTIFICATE OF CORRECTION

PATENT NO. : 4,953,976

DATED : September 4, 1990

INVENTOR(S) : Steven Adler-Golden, et al

It is certified that error appears in the above-identified patent and that said Letters Patent is hereby corrected as shown below:

ON TITLE PAGE: After Item [54], Insert

"The invention was made with Governmental support under NAS10-11379 awarded by NASA. The Government has certain rights in the invention."

Signed and Sealed this

Eleventh Day of February, 1992

Attest:

HARRY F. MANBECK, JR.

Attesting Officer

Commissioner of Patents and Trademarks